United States Patent
Bianco et al.

(10) Patent No.: US 6,420,374 B1
(45) Date of Patent: Jul. 16, 2002

(54) USE OF XANTHINES AS IMMUNOSUPPRESSANTS AND TO INHIBIT ALLOGRAFT REACTIONS

(75) Inventors: James A. Bianco; Jack W. Singer, both of Seattle, WA (US); William J. Novick, Jr., Lebanon, NJ (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 08/743,683

(22) Filed: Nov. 6, 1996

Related U.S. Application Data

(63) Continuation of application No. 08/193,608, filed on Feb. 7, 1994, now abandoned, which is a continuation of application No. 07/804,504, filed on Dec. 10, 1991, now abandoned, which is a continuation of application No. 07/620,480, filed on Nov. 30, 1990, which is a continuation of application No. 07/620,479, filed on Nov. 30, 1990.

(51) Int. Cl.$^7$ ............................................. A61K 31/52
(52) U.S. Cl. ...................................... 514/263; 514/264
(58) Field of Search ................................. 514/263, 264

(56) References Cited

U.S. PATENT DOCUMENTS

| | | |
|---|---|---|
| 3,422,107 A | 1/1969 | Mohler et al. |
| 3,737,433 A | 6/1973 | Mohler et al. |

(List continued on next page.)

FOREIGN PATENT DOCUMENTS

| | | |
|---|---|---|
| EP | 0005015 | 10/1979 |
| EP | 0036077 | 9/1981 |
| EP | 0063827 | 11/1982 |
| EP | 0173039 | 3/1986 |
| EP | 0310136 | 4/1989 |
| EP | 0313104 | 4/1989 |
| EP | 0344586 | 6/1989 |
| GB | 1441562 | 1/1975 |
| WO | WO 88/04928 | 7/1988 |

OTHER PUBLICATIONS

Gould Medical Dictionary, 3$^P$ edition, p. 856, 1972.*
Saki et al "Pentoxifylline–Induced Modulation . . . " *N. J. Path.* 136(3): 623–630 (1990).*
Shalaby et al., in "Involvement of Human Tumor Necrosis Factors–α and –β in the Mixed Lymphocyte Reaction," *J. Immunol.*, 141(2):99–503 (1988).
Imagawa et al., "The Role of Tumor Necrosis Factor in Allograft Rejection. I.," *Transplantation*, 50(2):219–225 (Aug. 1990).

(List continued on next page.)

*Primary Examiner*—Russell Travers

(57) ABSTRACT

A family of compounds effective in suppressing lymphocyte activation is comprised of 7-(oxoalkyl)1,3-dialkyl xanthines, other than denbufylline, of the formula

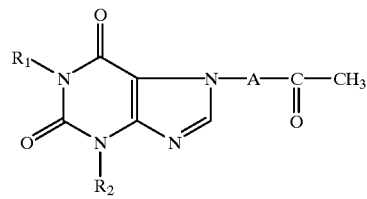

(I)

in which $R_1$ and $R_2$ are the same or different and are selected from the group consisting of straight-chain or branched alkyl radicals with 2 to 6 carbon atoms, cyclohexyl, alkoxyalkyl and hydroxyalkyl radicals, and A represents a hydrocarbon radical with up to 4 carbon atoms which can be substituted by a methyl group. Another family of effective compounds is comprised of compounds of the formula

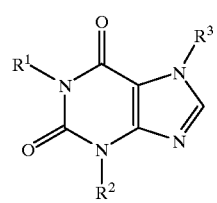

(II)

wherein at least one of $R_1$ and $R_3$ is either a) a branched hydroxyalkyl group of the formula

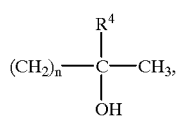

in which $R^4$ stands for an alkyl group with 1 to 3 carbon atoms and n stands for a whole number from 2 to 5, the other $R^1$ or $R^3$ group that lay optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or b) an oxoallyl group of the formula

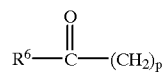

wherein $R^6$ is $C_1$–$C_6$ and p is 2, 3 or 4, the remaining $R^1$ or $R^3$ being as defined above, and $R^2$ is an alkyl group $C_1$–$C_4$; The suppression of lymphocyte activation is indicated in humans afflicted with autoimmune disease.

19 Claims, 2 Drawing Sheets

U.S. PATENT DOCUMENTS

| | | | |
|---|---|---|---|
| 4,225,607 A | | 9/1980 | Goring et al. |
| 4,242,345 A | | 12/1980 | Brenner et al. |
| 4,289,776 A | | 9/1981 | Mohler et al. |
| 4,372,959 A | | 2/1983 | Goring |
| 4,454,138 A | | 6/1984 | Goring |
| 4,511,557 A | | 4/1985 | Gauri |
| 4,515,795 A | | 5/1985 | Hinze et al. |
| 4,576,947 A | | 3/1986 | Hinze et al. |
| 4,636,507 A | * | 1/1987 | Kreutzer ..................... 514/263 |
| 4,657,910 A | | 4/1987 | Morgan |
| 4,719,212 A | | 1/1988 | Goto et al. |
| 4,784,999 A | | 11/1988 | Angersbach et al. |
| 4,833,146 A | | 5/1989 | Gebert et al. |
| 4,870,163 A | | 9/1989 | Rubin et al. |
| 4,871,663 A | | 10/1989 | Oshima et al. |
| 4,965,271 A | | 10/1990 | Mandell et al. |
| 5,096,906 A | | 3/1992 | Mandell et al. |

OTHER PUBLICATIONS

Imagawa et al., "The Role of Tumor Necrosis Factor in Allograft Rejection. II., " *Transplantation*, 50(2):189–193 (Aug. 1990).

Tilg et al., "Evaluation of Cytokines and Cytokine–Induced Secondary Messages in Sera of Patients After Liver Transplantation," *Transplantation*, 49(6):1074–1080 (Jun. 1990).

Irle et al., "Serum TNF Levels During Graft–Versus–Host Disease After Allogeneic Bone Marrow Transplantation," *Bone Marrow Transplantation*, 3(Suppl. 1):127 (1988).

Maury et al., "Raised Serum Levels of Cachectin/Tumor Necrosis Factor α in Renal Allograft Rejection," *J.Exp. Med.*, 166:1132–1137 (1987).

Shalaby et al., in "Prevention of the Graft–Versus–Host Reaction in Newborn Mice by Antibodies to Tumor Necrosis Factor–Alpha," *Transplantation*, 47(6):1057–1061 (Jun. 1989).

Imagawa et al., "Anti–Tumor Necrosis Factor Antibody Enhances Allograft Survival in Rats," *J. Surg. Res.* 48:345–348 (Apr. 1990).

Piguet et al., "Tumor Necrosis Factor/Cachectin is an Effector of Skin and Gut Lesions of the Acute Phase of Grafts–Vs.–Host Disease" *J. Exp. Med.*, 166:1280–1289 (1987).

Takei et al., "Video Microscopy of Transplanted Rat Livers," *Optical Microscopy for Biology*, Wiley–Liss, Inc. (1990), pp. 487–496.

Salyer et al., in "Mechanisms of Tumor Necrosis Factor–α Alteration of PMN Adhesion and Migration," *Am. J. Path.*, 136(4):831–841 (Apr. 1990).

Holler et al., "Increased Serum Levels of Tumor Necrosis Factor α Precede Major Complications of Bone Marrow Transplantation," *Blood*, 75(4):1011–1016 (Feb. 15, 1990).

McCord, J.M., "Oxygen–Derived Free Radicals in Postischemic Tissue Injury," *N. Eng. J. Med.*, 312(3):159–163 (1985).

Bessler et al., "Effect of Pentoxifylline on E–Rosette Formation and on the Mitogenic Response of Human Mononuclear Cells," *Biomed.& Pharmacother.*, 41:439–441 (1987).

Berman et al., "Pentoxifylline Inhibits Normal Human Dermal Fibroblast In Vitro Proliferation, Collagen, Glycosaminoglycan, and Fibronectin Production, and Increases Collagenase Activity," *J. Investigative Dermatol.*, 92:605–610 (Apr. 1989).

Bianco et al., *Blood* (1991) 78(5):1205–1211.

Singer et al., *Exp. Hermatol.* (1991) 19(6):553 (abstract No. 365).

Bianco et al., *Exp. Hematol.* (1991) 19(6):553 (abstract No. 366).

Kostakis et al., *IRCS Medical Science* (1982) 10(1):77–78.

Kostakis et al., *IRCS Medical Science* (1980) 8(1):15.

Rao et al., *FASEB J*. (1990) 4(3):A338 (abstract No. 420).

"The Merck Manual", 15th Edition, (1987) Merck & Co., Inc., pp. 322–329.

Bailly et al., *Int. J. Immunopharmacol.* (1990) 12(1):31–36.

Beutler et al., *Science* (1986) 232:977–980.

Bianco et al., Abstract Submission Form, Transplantation Society Meeting, (Aug. 1990) 1 page total.

Buja, *Trends in Cardiovascular Medicine* (Jan./Feb. 1991) pp. 40–49.

Bursten et al., *Biochemistry* (1991) 30:6195–6203.

Crumplin, *Reviews of Infectious Diseases* (1988) 10 (Supplement 1):S2–S9.

Endres et al., *Immunology* (1991) 72:56–60.

Fazely et al., *Blood* (1991) 77 (8):1653–1656.

Grunfeld et al., *Cancer Research* (1990) 50:4233–4238.

Han et al., *J. Exp. Med.* (1990) 172:391–394.

Heath et al., *Clinical Care Medicine* (1990) 18(7):766–767.

Hofmann et al., *J. Immunol.* (1990) 145(11):3699–3705.

Hooper et al., *Reviews of Infectious Disease* (1989) 11(Supplement 5):S902–SS911.

Josaki et al., *Amer. J. Pathol.* (1990) 136(3):623–630.

Lilly et al., *Amer. Rev. Respir. Dis.* (1989) 139:1361–1368.

Lindemann et al., *Blood* (1989) 73(4):880–884.

Matzky et al., *Arzneim.–Forsch./Drug Res.* (1982) 32:1315–1318.

Strieter et al., *Biochem. Biophys. Res. Commun.* (1988) 155(3):1230–1236.

Tracey et al., *The Lancet* (May 20, 1989) pp. 1122–1125.

Wilcox et al., *Trends in Cardiovascular Medicine* (Jan./Feb. 1991) pp. 17–28.

Zabel et al., *The Lancet* (Dec. 23/30, 1989) pp. 1474–1477.

*Clinical Immunology Spectrum* (Jun. 1991) p. 4.

*Onkologie* (Oct. 1991) 4(Supplement 2) 1 abstract page total.

* cited by examiner

USE OF XANTHINES AS IMMUNOSUPPRESSANTS AND TO INHIBIT ALLOGRAFT REACTIONS

CROSS-REFERENCE TO RELATED APPLICATION

This application is a continuation-in-part of application Ser. No. 07/620,479, filed Nov. 30, 1990, and entitled USE OF XANTHINES FOR INHIBITING THE EFFECTS OF ALLOGRAFT REACTION IN HUMANS, the entire disclosure of which is relied upon and incorporated by reference herein.

This is a Continuation of U.S. application Ser. No. 08/193,608, filed Feb. 7, 1994 which is a continuation of Ser No. 07/824,504 filed Dec. 10, 1991 now abandoned, is a Continuation of U.S. application Ser. No. 08/193,608, filed Feb. 7, 1994 now abandoned, which is a continuation of Ser. No. 07/804,504 filed Dec. 10, 1991 now abandoned.

This invention was supported, in part, by a grant from the National Institutes of Health: CA 18029. The United States Government may have certain rights in this invention.

BACKGROUND OF THE INVENTION

This invention relates to the use of xanthines as immune suppressants in mammals. In one embodiment of the invention the xanthines suppress the activation of lymphocytes in mammals. In another embodiment, this invention relates to the use of xanthines to inhibit the effects associated with autoimmune disease in humans.

The immune system of vertebrates protects them from disease-causing (pathogenic) microorganisms, such as bacteria and viruses, from parasites, and from cancer cells. The immune system specifically recognizes and selectively eliminates foreign invaders by a process known as the immune response.

The immune system has evolved to provide an organism that can respond specifically to a wide variety of antigens. In order for an immune response to occur following antigen challenge, antigen must not only be recognized by antigen specific lymphocytes, but this recognition event must lead to a variety of cellular responses. T lymphocytes, together with B lymphocytes, represent the two antigen specific components of the cellular immune system. The activation of resting T lymphocytes is critical to most immune responses, because cellular activation allows the cells to exert their regulatory or effector activities. During activation relatively quiescent cells undergo complex changes involving cell differentiation and proliferation.

The immune response that results in the neutralization and elimination of foreign invaders may also cause disease. Diseases involving the immune system can be grouped into two general classes. Deficiency diseases result when a component of the system fails to function. These diseases manifest themselves clinically by low resistance to infection and loss of immunologic surveillance functions. Hypersensitivity diseases result when the system reacts under inappropriate conditions. For example, immune responses to self components may lead to a breakdown in immunological tolerance causing autoimmune diseases. An autoimmune disease is one in which the body makes an immune response to one of its own constituent antigens, which then causes pathologic damage. A multiplicity of organs and tissues is involved in autoimmune disease. Autoimmunity is a major problem in clinical medicine and is the cause of great economic loss.

There exists a need in the art for means for controlling the immune response by suppressing the immune system in mammals. There also exists a need for the clinical management of hypersensitivity diseases, including autoimmune diseases in humans. Because the existing treatments and means for preventing autoimmune diseases are not entirely satisfactory, new approaches in preventing or treating such diseases must be found, since autoimmune diseases is a major cause of suffering in patients afflicted with immune response disorders.

SUMMARY OF THE INVENTION

This invention aids in fulfilling these needs in the art by providing a method of suppressing the activation of lymphocytes, including T lymphocytes and B lymphocytes, in mammals, such as humans. More particularly, this invention provides a method of suppressing activation of lymphocytes in a mammal by administering to the human at least one 7-(oxoalkyl) 1,3-dialkyl xanthine, other than denbufylline, of the formula:

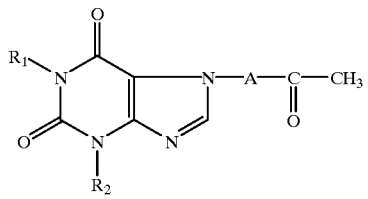

(I)

in which
  $R_1$ and $R_2$ are the same or different and are independently selected from the group consisting of straight-chain or branched-chain alkyl radicals with 2 to 6 carbon atoms, cyclohexyl, straight chain or branched chain alkoxyalkyl, and hydroxyalkyl radicals; and
  A is a hydrocarbon radical with up to 4 carbon atoms which can be substituted by a methyl group.
The xanthine of formula (I) is employed in an amount that is effective in suppressing lymphocyte activation.

This invention also provides a method of suppressing lymphocyte activation in a mammal, comprising administering to the mammal a compound of the formula:

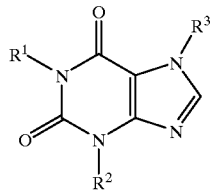

(II)

wherein at least one of $R^1$ and $R^3$ is either
  (a) a branched hydroxyalkyl group of the formula

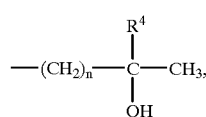

with a tertiary alcohol function, in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or (b) at least one of $R^1$ or $R^3$ is an oxoallyl group of the formula

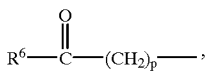

wherein $R^6$ is $C_1$–$C_6$ alkyl, and p 2, 3 or 4; the other $R^1$ or $R^3$ being defined as above and $R^2$ represents an alkyl group with 1 to 4 carbon atoms.

The xanthine of formula (II) is employed in an amount that is effective in suppressing lymphocyte activation. The well known pharmaceutical pentoxifylline is an example of a compound within the general formula (II). Pentoxifylline ("PTXX") is commercially available under the trademark Trentals in the form of tablets for oral administration. Although this compound has been used for time as a pharmaceutical to improve the flow properties of blood (clinical trials in 1971), it has not been reported effective as an inhibitor of lymphocyte activation.

BRIEF DESCRIPTION OF THE DRAWINGS

This invention will be more fully understood by reference to the Figures in which.

DETAILED DESCRIPTION OF PREFERRED EMBODIMENT

Figure 1:
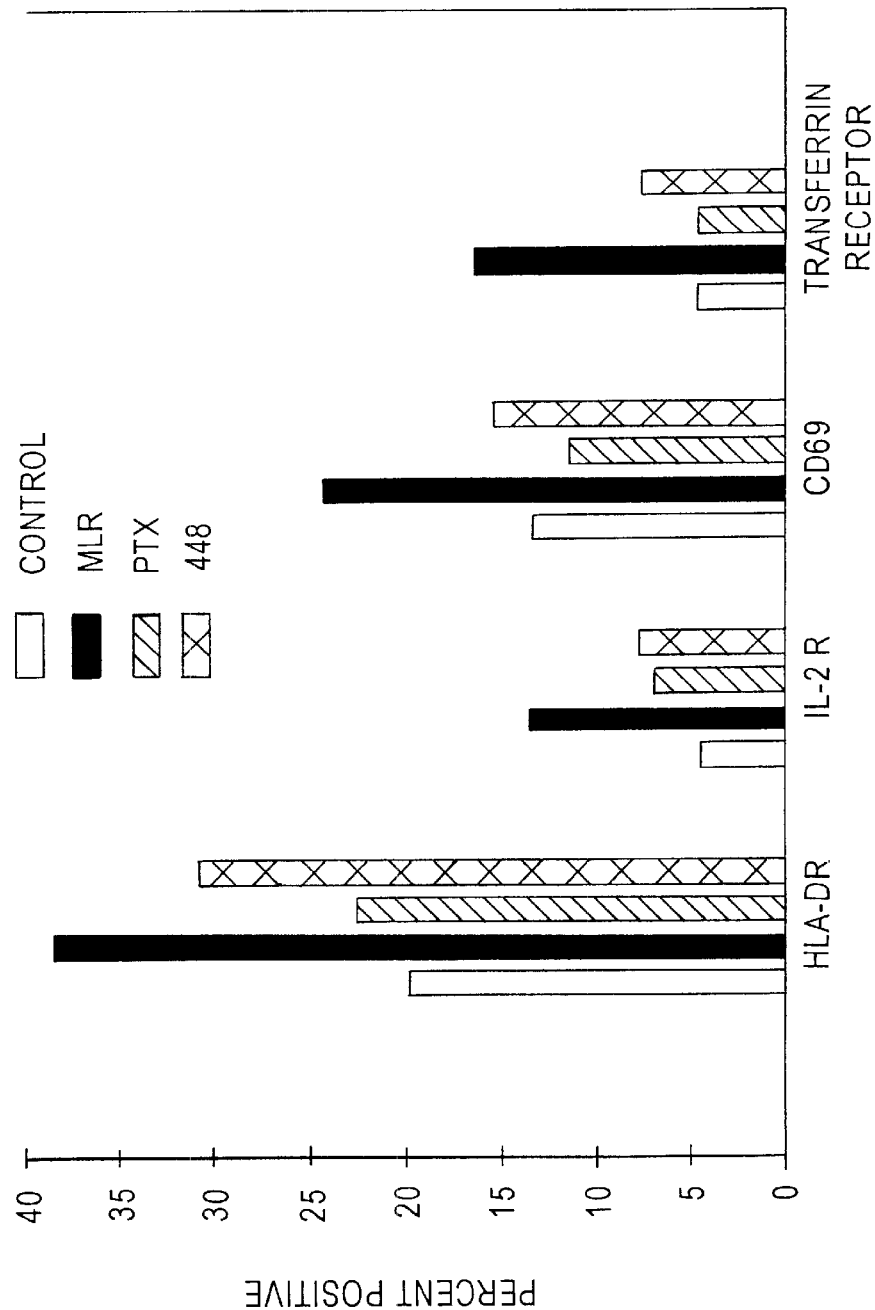
FIG. 1 shows the effect of PTX and 7-ethoxymethyl-1-(5-hydroxy-5-methylhexyl-3-methylxanthine on the expression of T cell activation antigens analyzed by direct immunofluorescence after 6 days of culture in a bidirectional MLR.

Certain xanthines are employed according to this invention to inhibit the responses of T lymphocytes to thereby suppress immune response in mammalian subjects. The nature of the biological processes involved in this invention will initially be described. This will be followed by a detailed description of the xanthines and methods for preparing the xanthines. The results obtained by in vitro testing will follow.

1. Xanthines as Immunosuppressants

The xanthines when employed according to the invention suppress activation or functioning of several types of effector cells (other than effector inflammatory cells). That is, the xanthines suppress activation of lymphocytes, namely T lymphocytes and B lymphocytes. More particularly, the xanthines are capable of suppressing activation of one or more lymphocytes selected from the group consisting of T helper cells, T cytotoxic cells, T suppressor cells, natural killer cells, killer cells responsible for antibody dependent cell-mediated cytotoxicity, T delayed hypersensitivity cells, B lymphocytes, and subsets of each of these cell types. Suppression of T cell activation by the xanthines can be demonstrated even in the absence of macrophages, neutrophils, and leukocyte-derived cytokines, such as tumor necrosis factor (TNF).

During the process of lymphocyte activation, B and T lymphocytes undergo a number of changes, including cell proliferation, cell differentiation, changes in membrane lipid, ion fluxes, cyclic nucleotide alterations, protein phosphorylations, increases or decreases in RNA synthesis of particular constitutive and newly activated genes, increases or decreases in protein synthesis of particular constitutive and newly activated gene products, cell volume increases (blast transformation), antibody production, or DNA synthesis. The xanthines are capable of suppressing one or more of these events when employed according to this invention.

Various parameters can be employed in experimental models to demonstrate lymphocyte activation. For example, lymphocyte activation can be determined by observing early signal transduction events, such as an increase in cytoplasmic free calcium; expression of cell surface antigens, such as interleukin 2 (IL-2) receptor and class II (MHC) molecules; production of lymphokines, such as IL-2; cell proliferation; or cytolytic activity. Lymphocyte activation as indicated by cell proliferation has been employed to demonstrate the effects of the xanthines accord- ing to this invention.

More particularly, co-cultivation of leukocytes from unrelated individuals leads to blast transformation and proliferation similar to that observed upon addition of mitogens to T-cells. The basis of this reaction appears to be the activation of T-cells from one individual by cell surface markers of another. Co-culturing of blood leukocytes from two individuals is referred to as "mixed leukocyte culture" or "MLC" and the reaction as "mixed leukocyte reaction" or "MLR". Co-culturing of cells obtained from lymphoid organs is designated "mixed lymphocyte culture" or "mixed lymphocyte reaction". Since even in the mixed leukocyte reaction, the participating cells are peripheral blood T lymphocytes, there is generally substantially no difference between the two types of culture. Thus, these expressions are used interchangeably herein.

MLR is utilized in this invention as the in vitro analog of lymphocyte activation in the human. More particularly, MLC can be employed in this invention as an in vitro assay for determining the preferred xanthines and the amount thereof to employ in a particular clinical setting. A xanthine that gives a strong response in inhibiting human MLR is preferred for use as an immunosuppressant according to this invention.

MLR can be carried out using conventional techniques. Cultured cells for the MLR can be derived from peripheral blood, spleen, lymph nodes, or thymus. Cell number can vary by several orders of magnitude. The stimulating cells can be inactivated by irradiation or treatment with an antibiotic to disrupt DNA replication. The culture medium can be supplemented, if necessary, by serum proteins of autologous, syngeneic, allogeneic, or xenogeneic origin. Cultivation can be carried out over a period of several days. The degree of stimulation of responder cells by stimulating cells can be determined from the uptake rate of $^3$H-thymidine or radiolabeled amino acids or by counting blasts and dividing cells. If a radiolabel is employed, it can be added to the culture several hours before harvesting.

The receptors on cell surfaces of lymphocytes have also been used as measures of the suppression of lymphocyte activation according to this invention. Xore particularly, a number of cell surface molecules appear on the surface of T lymphocytes during the events associated with activation, differentiation, and proliferation of T cells. These include lymphokine receptors, such as IL-2, nutrient receptors, class II MHC antigens, and other cell surface molecules. As the appearance of most of these cell surface molecules is transcriptionally regulated, the occurrence of these molecules can be employed as measures of cellular activation.

By suppressing the activation of lymphocytes, this invention also makes it possible to suppress the proliferation of autoantibodies. Autoantibodies are antibodies produced by an animal (or human) that bind to antigens present in its own cells or extracellular proteins. Autoantibodies operate through several pathogenic mechanisms, including receptor stimulation, receptor inhibition, formation of immune complexes, opsonization, complement-dependent lysis, and inhibition of physiological peptides. The use of xanthines according to this invention makes it possible to interrupt one or more of these pathogenic mechanisms.

The method of this invention is also useful for the treatment of human subjects afflicted with hypersensitivity disease, such as autoimmune disease. The autoimmune diseases that can be treated according to this invention include the organ specific autoimmune diseases, such as the following:

Endocrine system
    Autoimmune (Hashimoto's) thyroiditis
    Hyperthyroidism (Graves' disease, thy:rotoxicosis)
    Type 1 diabetes mellitus (insulin-dependent or juvenile diabetes)
    Insulin-resistant diabetes
    Autoimmune adrenal insufficiency (Addison's disease)
    Autoimmune oophoritis
    Autoimmune orchitis Hematopoietic system
    Autoimmune hemolytic anemia "warm" autoantibody type)
    Autoimmune hemolytic anemia (cold agglutinin disease)
    Paroxysmal cold hemoglobinuria
    Autoimmune thrombocytopenia
    Autoimmune neutropenia
    Pernicious anemia
    Pure red cell anemia
    Autoimmune coagulopathies (circulating anticoagulants)

Neuromuscular system
    Myasthenia gravis
    Autoimmune polyneuritis
    Multiple sclerosis
    Experimental allergic encephalomyelitis Skin
    Pemphigus and other bullous diseases Cardiopulmonary system
    Rheumatic carditis
    Goodpasture's syndrome (pulmonary hemorrhage and nephritis)
    Postcardiotomy syndrome (Dressler's syndrome)

The autoimmune diseases that can be treated according to this invention also include the systemic autoimmune diseases, such as:

Systemic lupus erythematosus
    Rheumatoid arthritis
    Sjogren's syndrome (keratitis, parotitis, and arthritis)
    Polymyositis
    Dermatomyositis
    Scleroderma (progressive systemic sclerosis).

The pathogenic mechanisms that provoke these two classes (organ specific and systemic) of autoimmune disease appear to be different. Highly relevant: to organ specific autoimmunization are tolerance and suppression within the T cell population, aberrant expression of MHC antigens, and variations in MHC genes. The pathogenesis of systemic autoimmune diseases may involve polyclonal B cell activation, as well as abnormalities of T cells, T cell receptor and MHC genes.

It will be understood that this invention can be employed as a minimal or aggressive immnlosuppressive therapy in a patient. More particularly, when the xanthines are employed according to this invention, they function as immunosuppressive agents by lowering immune response of the host. The xanthines can be employed according to the invention, either before, after, or simultaneously with the use of chemical immunosuppressive agents, such as alkylating agents, antimetabolites, corticosteroids, or antibiotics; physical immunosuppressive agents, such as ionizing radiation; immune reagents, such as antilymphocytic serum or antilymphocytic globulins; or by the administration of antigens or polyclonal or monoclonal antibodies for specific suppression.

More particularly, the xanthines can be administered before, during, or after the administration of immunosuppressive agents, such as cyclophosphamide, methotrexate, cyclosporin A, prednisone, methylprednisone, antithymocyte globulin, monoclonal antibodies reactive with human lymphocyte subpopulations, or combinations of these therapies. These immunosuppressants are employed according to the regimens usually used for immunosuppression.

Similarly, the xanthines can be employed according to the invention with the administration of corticosteroids, such as prednisone and methyl prednisone; cyclosporin A; azathioprine; antilymphocytic serum or globulin; monoclonal antibodies reactive with human lymphocyte subpopulations; or combinations of these therapies. Once again, these immunosuppressants are employed according to the regimens usually used for immunosuppression.

This invention also makes it possible to inhibit the effects of allograft reaction in human subjects. More particularly, xanthines are employed according to this invention to modulate the immune responses to allografts where untreated rejection would otherwise leadc to graft loss. Acute graft rejection is predominantly a cell-mediated immune response.

Allograft reaction can be manifested as host versus graft reaction (HVGR) or as graft versus host reaction (GVHR) in human subjects. HVGR can lead to graft failure or rejection due to host resistance or persistent host immunity. Host cells may impair the engraftment oil donor-derived tissue or the proliferation and differentiation of donor-derived cells.

The use of xanthines according to this invention makes it possible to increase the feasibility of transplant procedures. The xanthines are valuable therapeutic agents for both prophylaxis and treatment of allograft reaction, such as HVGR and GVHD. Survival following engraftment is primarily related to the severity of acute GVHD. This invention makes it possible to inhibit GVHR, and a related reduction in GVHD is anticipated.

2. Administration of Xanthines to Human Patients

Effective amounts of the xanthines can be administered to a subject by any one of various methods, for example, orally as capsules or tablets, or parenrterally, such as by intravenous or intramuscular injection, in the form of sterile solutions. The xanthines, while effective themselves, can be formulated and administered in the form of their pharmaceutically acceptable addition salts for purposes of stability, convenience of crystallization, increased solubility, and the like.

Preferred pharmaceutically acceptable addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as, maleic acid, fumaric acid, oxalic acid, and the like; and salts of tribasic carboxylic acids, such as, carboxysuccinic acid, citric acid, and the like.

The xanthines can be administered orally, for example, with an inert diluent or with an edible carrier. They can be enclosed in gelatin capsules or compressed into tablets. For the purpose of oral therapeutic administration, the compounds can be incorporated with excipients and used in the form of tablets, troches, capsules, elixirs, suspensions, syrups, wafers, chewing gums, and the like. These preparations should contain at least 0.5% of active compound, but the amount can be varied depending upon the particular form and can conveniently be between 4.0% to about 70% of the weight of the unit. The amount of xanthine in such compositions is such that a suitable dosage will be obtained. Preferred compositions and preparations according to the present invention are prepared so that an oral dosage unit form contains between about 1.0 mgs and about 400 mgs of active compound.

Tablets, pills, capsules, troches, and the like can contain the following ingredients: a binder, such as microcrystalline cellulose, gum tragacanth or gelatin; an excipient, such as starch or lactose; 2a disintegrating agent, such as alginic acid, Primolgel, corn starch, and the like; a lubricant, such as magnesium sterate or Sterotes; a glidant, such as colloidal silicon dioxide; a sweetening agent, such as sucrose or saccharin; or flavoring agent, such as peppermint, methyl salicylate, or orange flavoring. When the dosage unit form is a capsule, it can contain, in addition t-material of the above type, a liquid carrier, such as a fatty oil.

Other dosage unit forms can contain other materials that modify the physical form of the dosage unit, for example, as coatings. Thus, tablets or pills can be coated with sugar, shellac, or other enteric coating agents. A syrup can contain, in addition to the active compounds, sucrose as a sweetener, and preservatives, dyes, colorings, and flavors. Materials used in preparing these compositions should be pharmaceutically pure and non-toxic in the amounts used.

For purposes of parenteral therapeutic administration, the xanthines can be incorporated into a solution or suspension. These preparations should contain at least 0.1% of the aforesaid compound, but may be varied between 0.5% and about 50% of the weight thereof. The amount of active compound in such compositions is such that a suitable dosage will be obtained. Preferred compositions and preparations according to the present invention are prepared so that a parenteral dosage unit contains between 0.5 mg to 100 mgs of the active compound.

Solutions or suspensions of the xanthines can also include the following components: a sterile diluent, such as water for injection, saline solution, fixed oils, polyethylene glycols, glycerine, propylene glycol or other synthetic solvents; antibacterial agents;, such as benzyl alcohol or methyl parabens; antioxidants, such as ascorbic acid or sodium bisulfite; chelating agents, such as ethylenediaminetetraacetic acid; buffers, such as acetates, citrates, or phosphates; and agents for the adjustment of tonicity, such as sodium chloride or dextrose. The parenteral preparation can be enclosed in ampoules, disposable syringes, or multiple dose vials made of glass or plastic.

While dosage values will vary, good results are achieved when the xanthines of formula (I) or formula (II) are administered to a subject requiring such treatment as an effective oral, parenteral, or intravenous sublethal dose of about 1,200 to about 2,400 mg per day. A particularly preferred regimen for use in bone marrow transplant therapy comprises the intravenous administration of PTX in aqueous saline solution (100 mg/5 ml) at ½ mg/kg/hour continuously for 20 days, followed by 2,000 mg/day oral dosage to day 100 post-transplant. It is to be understood, however, that for any particular subject, specific dosage regimens should be adjusted to the individual need and the professional judgment of the person administering or supervising the administration of the xanthines. It is to be further understood that the dosages set forth herein are exemplary only and that they do not, to any extent, limit the scope or practice of the invention.

3. Descriotion and Preparation of Xanthines of Formula (I)

One group of xanthines that can be employed in this invention has the following formula:

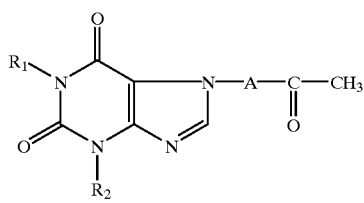

(I)

The substituents $R_1$ and $R_2$ in formula (I) are the same or different and are independently selected from the group consisting of straight-chain or branched alkyl radicals with 2 to 6 carbon atoms, cyclohexyl, alkoxyalkyl, and hydroxyalkyl radicals. The substituent: A represents a hydrocarbon radical with up to 4 carbon atoms, which can be substituted by a methyl group.

A number of compounds of formula (I) can be employed in this invention. For example, the xanthines of formula (I) can be substituted by alkyl groups or by alkoxy or hydroxyalkyl groups. Suitable alkyl groups include branched and straight chain groups, such as ethyl, propyl, isopropyl, butyl, sec-butyl, tert-butyl, amyl, hexyl, and the like. Alkoxy substituted alkyl groups include branched and straight chain groups containing from 2 to 6 carbon atoms in the combined alkoxy and alkyl groups, including methoxymethyl, amyloxymethyl, methoxyethyl, butoxyethy:L, propoxypropyl, and the like. Hydroxyalkyl groups are those containing from 1 to 6 carbon atoms, such as hydroxymethyl, hydroxyethyl, hydroxypropyl, hydroxyhexyl, and the like.

The hydrocarbon groups represented by A in formula (I) are divalent saturated aliphatic hydrocarbon groups, i.e., methylene, ethylene, trimethylene and tatramethylene, which can be substituted on the carbon adjacent the carbonyl group with methyl. Such methyl-substituted groups include ethylidine, 1,2-propylene, and 1,3-butylene groups.

It will be understood that the method of this invention can be practiced with compounds that change in vivo into one of the aforementioned xanthines of formula (I), as well as compounds that produce metabolites in vivo similar to the metabolites formed from the aforementioned xanthines of formula (I).

A compound within formula (I) that has been found to be not effective in suppressing lymphocyte activation is denbufylline. This compound, which is also referred to herein in abbreviated form as "DBOPX", has the following formula:

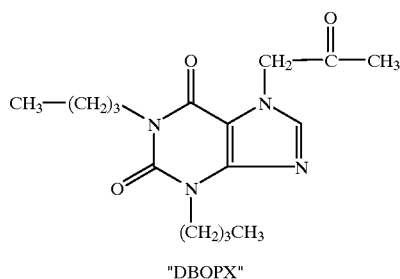

"DBOPX"

The ability of compound (III) in suppressing lymphocyte activation evidenced by MLR has not been demonstrated in vitro.

The compounds of formula (I) employed in this invention can be synthesized using known techniques. For example, the compounds can be prepared at elevated temperature, optionally in the presence of a solvent, by reacting correspondingly substituted 1,3-dialkyl xanthines of the formula (III)

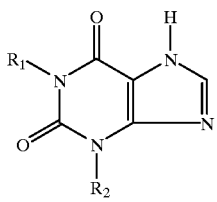

in which $R_1$ and $R_2$ are as defined above, with a, β-unsaturated methyl ketones corresponding to the formula (IV)

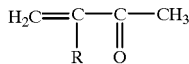

The substituent R in formula (IV) represents hydrogen or a methyl group. The reaction can be conducted in an alkaline medium.

An alternative method of preparation involves reacting alkali metal salts of 1,3-dialkyl xanth.ine derivatives of general formula II, in which $R_1$ and $R_2$ are as defined above, with oxoalkyl halides corresponding to the formula (V)

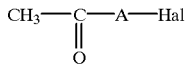

in which A is as defined above, and Hal represents a halogen atom, preferably chlorine or bromine.

These reactions are preferably carried out at temperatures in the range from 40° to 80° C., optionally under elevated or reduced pressure, but usually at atmospheric pressure. The individual starting compounds can be employed either in stoichiometric quantities or in excess. The alkali salts in the alternative method of preparation can either be prepared beforehand or in the reaction itself.

Suitable solvents for use in the reactions are water-miscible compounds, preferably lower alcohols, such as methanol, propanol, isopropanol, and various butanols; also acetone; pyridine; triethylamine; polyhydric alcohols, such as ethylene glycol and ethylene glycol monomethyl or monethyl ether.

The compounds of formula (I) are known for their marked effect in increasing blood flow through skeletal muscle and by their low toxicity. A more detailed description of the compounds employed in this invention and methods of preparing the compounds are contained in U.S. Patent 4,242,345, the entire disclosure of which is relied upon and incorporated by reference herein.

4. Description and Preparation of Xanthines of Formula (II)

Inhibition of allograft reaction, and in particular GVHR, can also be achieved by administering to a human patient a xanthine of the formula:

(II)

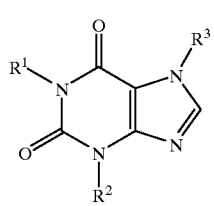

wherein at least one of $R^1$ and $R_3$ is either (a) a branched hydroxyalkyl group of the formula

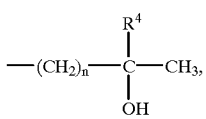

with a tertiary alcohol function, in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or (b) at least one of R or $R^3$ is an oxoallyl group of the formula

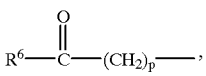

wherein $R^6$ is $C_1-C_6$ alkyl, and p=2, :3 or 4; the other $R^1$ or- $R^3$ being defined as above, and $R^2$ represents an alkyl group with 1 to 4 carbon atoms. The xanthine of formula (II) is employed in an amount that is effective in inhibiting allograft reaction, especially GVHR. Among these compounds is the commercially available TRENTAL® (pentoxifylline) Tablets. A host of other compounds within the general formula (II) can be employed for inhibiting GVHR activity. Among these compounds are those identified below.

GVHR-INHIBITING COMPOUNDS OF FORMULA (II)

| Compound Number | $R_1$ | $R_2$ | $R_3$ |
|---|---|---|---|
| 2 | $CH_3-CO-(CH_2)_4-$ | $-CH_3$ | $-CH_2-CH_2-CH_3$ |
| 3 | $CH_3-C(OH)(CH_3)-(CH_2)_4-$ | $-CH_3$ | $-CH_2-CH_2-O-CH_3$ |
| 4 | $CH_3-C(OH)(CH_3)-(CH_2)_4-$ | " | $-CH_2O-(CH_2)_2-O-CH_3$ |
| 5 | $CH_3-C(OH)(CH_3)-(CH_2)_4-$ | " | $-H$ |
| 6 | $CH_3-C(OH)(CH_3)-(CH_2)_4-$ | " | $-CH_2-CH_2-CH_3$ |
| 7 | $CH_3-C(OH)(CH_3)-(CH_2)_4-$ | " | $-CH_2-CH(OH)-CH_3$ |
| 8 | $CH_3-C(OH)(CH_3)-(CH_2)_4-$ | " | $-CH_2-CH(OH)-(CH_3)_2$ |
| 9 | – | $-CH_2-CH_3$ | $-CH_2-O-CH_2-CH_3$ |
| 10 | $CH_3-C(OH)(CH_3)-(CH_2)_4-$ | $-CH_3$ | $-(CH_2)_4-C(CH_3)(OH)-CH_3$ |
| 11 | $CH_3-C(OH)(CH_3)-(CH_2)_4-$ | " | $-CH_2-O-CH_2-CH_3$ |

It will be understood that the method of this invention. can be practiced with compounds that change in vivo into one of the aforementioned xanthines of formula (II), as well as compounds that produce metabolites in viva similar to the metabolites formed from the aforementioned xanthines of formula (II). For example, after oral and intravenous administration, pentoxifylline is almost completely metabolized. The following seven metabolites have been identified in human urine, which is the predominant pathway for excretion of metabolites:

Metabolite I 1-(5-hydroxyhexyl)-3,7-dimethylxanthine
Metabolite II 1-(5,6-dihydroxyhexyl)-3,7-dimethylxanthine
Metabolite III 1-(4,5-dihydroxyhexyl)-3,7-dimethylxanthine
Metabolite IV 1-(4-carboxybutyl)-3,7-dimethylxanthine
Metabolite V 1-(3-carboxypropyl)-3,7-dimethylxanthine
Metabolite VI 1-(5-oxohexyl)-3-methylxanthine
Metabolite VII 1-(5-hydroxyhexyl)-3-methylxanthine.

Metabolites I and v are the major metabolites. Metabolite V, the main urinary Metabolite, accounts for about 50–60 percent of the administered dose. Only traces of pentoxifylline and Metabolite I are found in urine. The dihydroxy derivatives of pentoxifylline (Metabolites II and III) represent approximately 12 percent and Metabolite IV about 8 percent of the excretion products.

The compounds of formula (II) can be prepared according to the disclosure of U.S. Pat. No. 3,737,433 and Belgium Patent 831,051 (where $R^1/R^3$ are oxoallyl). For the case where at least one of $R^1/R^3$ is a tertiary alcohol reference may be had to International Application PCT/EP86/00401, filed Jul. 8, 1986, claiming German priority of Jul. 8, 1985. This application addresses, as its invention, a variety of embodiments of synthesis routes for the xanthines of formula (II) embraced in the current invention.

An example of one embodiment consists of a) reacting 3-alkylxanthines of formula (VII)

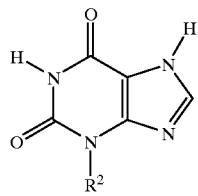
(VII)

in which the $R^3$ represents alkyl with up to 4 carbon atoms, with alkylating agents of formula (VIII:)

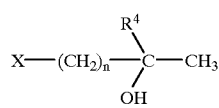
(VIII)

in which X stands for halogen, preferably chlorine, bromine, or iodine, or a sulfonic acid ester group or a phosphoric acid ester group, and wherein $R^4$ and n have the meanings mentioned above, to obtain compounds of formula (IX)

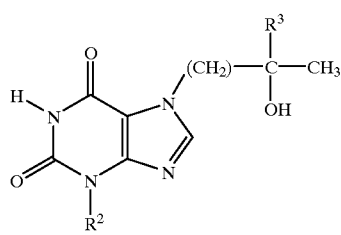
(IX)

with a tertiary hydroxyalkyl group in the position of $R^3$ and hydrogen in the position of $R^1$, and a₁) alkylating this with the sane or different alkylating agent of formula (VIII) to obtain compounds pursuant to the invention of formula (X)

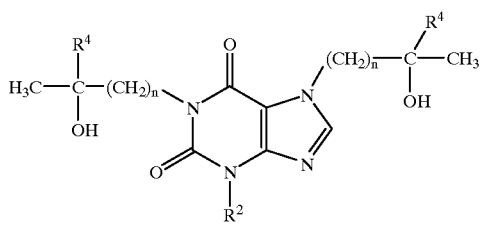
(X)

with two identical or different tertiary hydroxyalkyl groups in the positions of $R^1$ and $R^3$, or a₂) converting it with a compound of the formula $$R^5\text{---}X \quad (Xa)$$

in which X has the meaning given in formula (VIII) and $R^5$ has the meaning indicated above, into compounds of formula (XI)

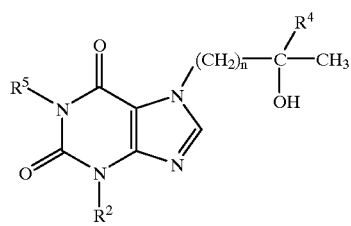
(XI)

in all cases preferably operating in the presence of basic media or using the xanthines in the form of their salts.

Another embodiment consists of b) substituting 1,3-dialkylated xanthines of formula (XII)

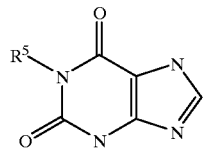
(XII)

in the 7-position, preferably in the presence of basic media or in the form of their salts, by one-step reaction with a compound of formula (VIII), to obtain compounds of formula (XI).

Another embodiment consists of c) first reacting the 3-alkylxanthines of formula (VII), likewise preferably in the presence of basic media or in the form of their salts, with a compound of the formula $$R^{15}\text{---}X \quad (XIII)$$

with the formation of 3,7-disubstituted xanthines of formula (XIV)

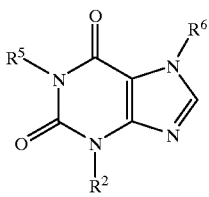
(XIV)

in which $R^{15}$ has the meaning mentioned for $R^5$ or stands for benzyl or diphenylmethyl, and then substituting them in the 1-position, again preferably in the presence of basic media or in the form of their salts, with a compound of formula (VIII). Compounds of formula (XV) are obtained

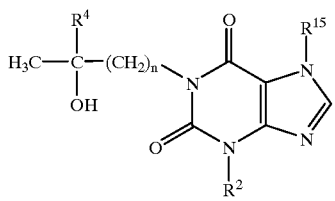
(XV)

in which $R^{15}$ represents a benzyl or diphenylmethyl, and converting the compounds of formula (XV) in which $R^{15}$ represents a benzyl or diphenylmethyl group or an alkoxymethyl or alkoxyalkoxymethyl group, under reducing or hydrolytic conditions, into compounds pursuant to the invention of formula (XVI)

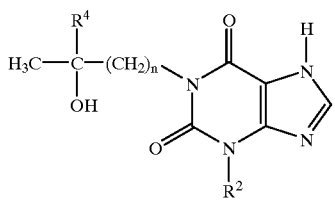
(XVI)

that are subsequently reacted again, if desired, with a compound of formula (VIII) or (Xa) to obtain compounds pursu- ant to the invention of formula (X) or (XV).

Another embodiment consists of d) reducing compounds of formula (XI) or (XV) pursuant to the invention in which $R^5$ or $R^{15}$ stands for an oxoalkyl group, with conventional reducing agents for the keto group to obtain the corresponding hydroxyalkylated xanthines pursuant to the invention.

The 3-alkyl- or 1,3-dialkyixanthin[]es of formula (VII) or (XII) used here as starting materials and the "alkylating agents" of formulas (VIII), (Xa), and (XIII) are known for the most part or can be prepared readily by methods disclosed in the literature. Thus, the tertiary alcohols of formula (VIII), for example, can be obtained by organometallic synthesis by reacting the sterically unhindered haloketones of the formula

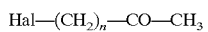
(XVII)

in a so-called synthetic reaction with reductive alkylation of the carbonyl group, with alkylmetal compounds $R^4$—M, especially of magnesium, zinc, or lithium, for example in the form of alkylmagnesium halides $R^4$—MgHal (Grignard compounds) or of the alkyllithium compounds $R^4$—Li, under the usual conditions (for example, see Houben-Weyl., Vol. VI/1 a, Part 2 (1980), pp. 928–40, especially pp. 1021 ff. and 1104–1112). In the same way, a reaction of the halok:etones with the formula

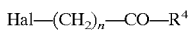
(XVIII)

with methylmagnesium halides or methyllithium likewise leads to the target.

The hydroxyketones corresponding to the formulas (XVII) and (XVIII) can also be converted smoothly into diols with the alkylmetal compounds in the usual way, either directly or with temporary masking of the hydroxy group, for example by acetal formation with 5,6-dihydro-4H-pyran (for example, see Houben-Weyl, Vol. VI/1 a, Part 2 (1980), pp. 1113–1124), from which compounds of formula (VIII) are formed by selective esterification of the terminal primary hydroxyl groups with sulfonyl or phosphoric halides or anhydrides, advantageously in the presence of basic media.

Other possibilities for the synthesis of the tertiary alcohol derivatives of formula (VIII) consist of the monometallation of ω-chloro-1-bromooalka[]nes to obtain ω-chloroalkylmetal compounds, (Houben-Weyl., Vol. XIII/2 a (1973), pp. 102 and 319) and their subsequent reaction with the ketones $R^4$—CO—$CH_3$, with the extent of by-product formation from the alkanolates formed as intermediates because of their tendency toward ring closure with the elimination of metal salt being minimized by appropriate temperature control, or of using ω-halo-1-alkanols as starting materials, which are metallated in the usual way, preferably in the form of the tetrahydropyranyl-(2) ether or after alkanolate formation of the hydroxy group (MO—$CH_2$)$_n$—Hal) with any desired alkylmetal compound (for example, see Houben-Weyl, Vol. XIII/2 a (1973), p. 113), then reacting them with the ketones $R^4$—CO—$CH_3$ to obtain the diols mentioned in the preceding paragraph (Houben-Weyl, Vol. VI/1 a, Part 2 (1980), p. 1029), and subsequently selectively esterifying the primary hydroxy group with suitable sul:E-onic or phosphoric acid derivatives.

A convenient access to compounds of formula (VIII) in which $R^4$ represents a methyl group is also available through the reaction of ω-haloalkanoic acid alkyl esters (Hal—$(CH_2)_n$—COO-alkyl) with two equivalents of a methylmetal compound, with the ester reacting through the ketone to produce the tertiary alcohol with the introduction of two methyl groups (Houben-Weyl, Vol. VI/1 a, Part 2 (1980), pp. 1171–1174). In the same way, w-hydroxy-carboxylic acid esters can be converted into diols with methylmetal compounds with or without protection of the hydroxy group, for example in the form of tetrahydropyranyl-(2) or methoxymethyl ester, or optionally in the form of the lactones as cyclic esters (for example, see Houben-Weyl, Vol. VI/1 a, Part 2 (1980), pp. 1174–1179), from which active alkylating agents of formula (VIII) can in turn be obtained by selective esterification of the primary hydroxyl group with sulfonic or phosphoric halides or anhydrides.

Suitable compounds of formula (VIII) that can be prepared by the methods described above are thus the [(ω-1)-hydroxy-(ω-1)-methyl]butyl, -pentyl, -hexyl, and -heptyl, the [(ω-2)-hydroxy-(ω-2)-methyl]pentyl, -hexyl, and -octyl, and the [(ω-3)-hydroxy-(ω-3)-methyl]hexyl, -heptyl, -octyl, and -nonyl chlorides, bromides, iodides, sulfonates, and phosphates.

Among the compounds of formula $R^5$—X (Xa) or $R^{15}$—X (XIII) suitable for the introduction of $R^5$ into the 1- or 7-positiorr and of $R^{15}$ into the 7-position of the xanthine skeleton, the alkoxymethyl and alkoxyalkoxymethyl derivatives occupy a special position as their halides can indeed be used successfully as reactants, but toxicological problems can arise, at least in large-scale use. For this reason, the use of the corresponding sulfonates is preferred in this special case, which are readily available, for example, by reacting mixed anhydrides of aliphatic carboxylic acids and aliphatic or aromatic sulfonic acids (M. H. Karger et al., J. Org. Chem. 36 (1971), pp. 528-531) with the formaldehyde dialkyl acetals or dialkoxyalkyl acetals in a smooth and nearly quantitative reaction (M. H. Karger et al., J. Amer. Chem. Soc. 91 (1969), pp. 5663/5665:

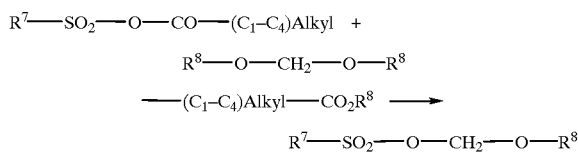

In this equation, $R^7$ represents an aliphatic group such as methyl, ethyl, or trifluoromethyl, or an aromatic group, for example, phenyl, 4-tolyl, or 4-bromophenyl, but preferably methyl or 4-tolyl, and $R^8$ represents an alkyl or alkoxyalkyl group falling under the definition of $R^5$ or $R^{15}$.

The reaction can be carried out either in the substance or in an anhydrous aprotic solvent inert to the reactants at temperatures between −20° and +40° C., preferably between 0° and 20° C. No intermediate isolation of the highly reactive sulfonates, which are sensitive to hydrolysis and thermally labile, is necessary; they are preferably used immediately as crude products for the substitution on the nitrogen of the xanthines, with the usual addition of a basic condensing agent being unnecessary.

The reaction of the mono- or disubstituted xanthine derivatives, (IX), (XVI), (VII), (VIII) or (Xa) or (XIII) is ordinarily done in a distributing agent or solvent inert to the reactants. Practical representatives are especially dipolar, aprotic solvents, for example formamide, dimethylformamide, dimethyl-acetamide, N-methylpyrrolidone, tetramethylurea, hexamethylphosphoric t:riamide, dimethyl- sulfoxide, acetone, or butanone; however, alcohols such as methanol, ethylene glycol, and their mono- or dialkyl ethers with the alkyl group having 1 to 4 carbon atoms but both together having a maximum of 5 carbon atoms, ethanol, propanol, isopropanol, and the various butanols; hydrocarbons such as benzene, toluene, or xylenes; halogenated hydrocarbons, such as dichloromethane or chloroform; pyridine, and mixtures of the solvents mentioned or their mixtures with water can also be used.

The "alkylation reactions" are suitably carried out in the presence of a basic condensing agent. Examples of materials suitable for this are alkali metal or alkaline earth hydroxides, carbonates, hydrides, alcoholates, and organic bases, such as trialkylamines (L-or example, triethyl- or tributylamine), quaternary ammonium or phosphonium hydroxides and crosslinked resins with fixed, optionally substituted ammonium or phosphonium groups. The xanthine derivatives can also be used in the alkylation reaction directly in the form of their separately prepared salts, such as the alkali metal, alkaline earth, or optionally substituted ammonium or phosphonium salts. The mono- and disubstituted xanthine derivatives can also be alkylated either in the presence of the aforementioned inorganic condensing agents or in the form of their alkali metal or alkaline earth salts with the assistance of so-called phase transfer catalysts, for example tertiary amines, quaternary Ammonium or phosphonium salts, or crown ethers, preferably in a 2-phase system under the conditions of phase transfer catalysis. Among the suitable phase transfer catalysts that are generally commercially available are tetra ($C_1$–$C_4$)alkyl- and metyltrimethylammonium and -phosphonium salts, methyl-, myristyl-, phenyl-, and benzyltri ($C_1$–$C_4$)alkyl- and cetyltrimethylammonium as well as ($C_1$–$C_{12}$)alkyl- and benzyltriphenylphosphonium salts, with the compounds that have the larger and more symmetrically structured cation generally proving to be the more effective.

The introduction of the groups la, $R^5$, and $R^{15}$ by the procedures described above is generally carried out at a reaction temperature between 0° C. and the boiling point of the particular reaction medium used, preferably between 20° and 130°, optionally at elevated or reduced pressure, for which the reaction time can amount to less than 1 hour or up to several hours.

The reaction of the 3-alkylxanthines (VIII) to produce the compounds pursuant to the invention of formula (X) requires the introduction of two tertiary hydroxyalkyl groups. Either identical or different substituents can be linked to the xanthine skeleton in succession, or two identical hydroxyalkyl groups can be linked without isolation of intermediates in a single-pot reaction.

The reductive cleavage of the benzyl and diphenylmethyl group from compounds of formula (XV) with the formation of the xanthine atom in the 7-position, is carried Out under standard conditions that were developed especially in the framework of the protective group technique in alkaloid and peptide syntheses and can thus be assumed to be widely known. Besides the chemical reduction, particularly of the benzyl compounds with sodium in liquid ammonia (Houben-Weyl, Vol. XI/1 (1957), pp. 974–975), the elimination of the two aforementioned aralkyl groups by catalytic hydrogenolysis using a precious metal catalyst is also especially practical (Houben-Weyl, Vol. XI/1 (1957), pp. 968–971 and Vol. IV//1 c, Part I (1980), pp. 400–404). A lower alcohol is ordinarily used here as the reaction medium (optionally with the addition of formic acid or ammonia), or an aprotic solvent such as dimethylformamide or particularly glacial acetic acid; however, their mixtures with water can also be used. Especially suitable hydrogenation catalysts are palladium black and palladium on activated charcoal or barium sulfate, while other precious metals such as platinum, rhodium, and ruthenium frequently give rise to side reactions because of competitive ring hydrogenation and are therefore only conditionally usable. The hydrogenolysis is preferably carried out at temperatures between 20° C. and 100° C. and at atmospheric pressure, or preferably slight excess pressure up to approximately 10 bar, with reaction times of a few minutes to several hours generally being needed.

The 1,3,7-trisubstituted xanthines of formula (Xv) that have an alkoxymethyl or alkoxyalkoxymethyl group in the position of $R^{15}$ represent O,N-acetals. Consequently, their substituents in the 7-position can be split off under the usual conditions of acid hydrolysis (cf. Houben-Weyl, Vol. VI/I b (1984), pp. 741–745), with the 7H compounds of formula (XVI) likewise being formed. Examples of preferred groups that can be eliminated hydrolytically are the methoxy, ethoxy and propoxymethyl groups as well as the methoxyethoxy- and ethoxyethoxymethyl groups. The reaction is advantageously carried out with heating in dilute mineral acids such as hydrochloric or sulfuric acid, optionally with the addition of glacial acetic acid, dioxane, tetrahydrofuran, or a lower alcohol as a solution promoter.

Also useful are perchloric acid or organic acids, such as trifloroacetic, formic, and acetic acid, in combination with catalytic amounts of mineral acids. The alkoxyalkoxymethyl compounds in particular can also be cleaved by using Lewis acids, such as zinc bromide and titanium tetrachloride in anhydrous medium, preferably in dicholoromethane or chloroform, with the 7-bromomethyl or 7-bromozinc derivatives formed as intermediates hydrolyzing spontaneously during the aqueous workup. In the cleavage in mineral acid solution, the reaction temperature must be chosen so that no significant dehydration of the tertiary hydroxyalkyl group in the 1-position occurs; it should therefore be below 100° C. as a rule.

The reduction of the xanthines of formulas (XI) and (XV) with an oxoalkyl group in the position of $R^5$ or $R^{15}$ to the corresponding hydroxyalkyl compounds can indeed take place in principle either with base metals or by catalytic hydrogenation, but the method of choice consists of the reaction occurring under the very mild conditions and in high yields with simple metal hydrides ($MH_n$), complex metal hydrides ($M^1[M^2H_n]m$), or organometallic hydrides (Houben-Weyl, Vol. IV/1 d (1981), pp. 267–282, and Vol. VI/1 b (1984), pp. 141–155). Of the numerous complex metal hydrides that can be used for the reduction of ketones, the most frequently used reagents might be mentioned, for example, lithium alanate, lithium borohydride, and especially sodium borohydride, that is easier to handle because of its lower reactivity and above all permits working in alcoholic, alcoholic aqueous, and pure aqueous solutions or suspensions. In addition to the otherwise customary inert solvents, such as ethers (for example, diethyl ether, tetrahydrofuran, 1,2-dimethoxyethane), hydrocarbons and pyridine, nitriles, such as acetonitrile, can also be used as the reaction medium. The hydrogenation, which is suitably carried out at temperatures between 0° C. and the boiling point of the particular solvent, but preferably at room temperature, generally occurs rapidly and is complete within several minutes to a few hours.

The tertiary hydroxyalkylxanthines of formula (II) can also be prepared by reacting substituted xanthines of formula (XIX)

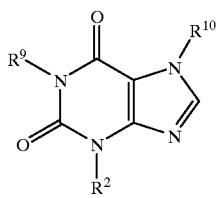

(XIX)

e) contains two identical or different groups of the formula

—$(CH_2)_n$—CO—$CH_3$ (XX); or

—$(CH_2)_n$—CO—$R^4$ (XXI), or only one substituent of the formula (XX) or (XXI), and hydrogen or the group $R^5$ or $R^{15}$ in the positions of $R^9$ and $R^{10}$, with ($C_1$–$C_3$)alkyl- or methylmetal compounds with reductive "alkylation" of the carbonyl groups to obtain the xanthines pursuant to the invention of formulas (IX) to (XVI), or f) metallating xanthines of formula (XIX) that have two identical or different groups of the formula —$(CH_2)_n$—Hal (XVII), with Hal preferably standing for chlorine or bromine, or only one such group and hydrogen or the substituent $R^5$ or $R^{15}$ in the other position, in the terminal position, and then reacting them with the ketones of the formula $R_4$—CO—$CH_3$ (XVIII)

with reductive alkylation of the carbonyl group to obtain the xanthines of formulas (IX) to (XVI) pursuant to the invention, or g) converting xanthines of formula (XIX) with the group —$(CH_2)_n$—COO—($C_1$–$C_4$)alkyl (XXIV)

in the positions of $R^9$ and/or $R^{10}$ and optionally hydrogen or the group $R^5$ or $R^{15}$ in the other position, by means of two equivalents of a methylmetal compound per alkoxycarbonyl group, into xanthines of formulas (IX) to (XVI) in which $R^4$ stands for methyl, or h) converting xanthines of formula (XIX) having two identical or different groups of the formula

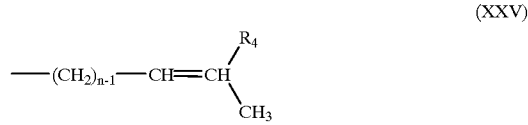

(XXV)

or only one such group and hydrogen or the group $R^5$ or R15 in the positions of $R^9$ and $R^{10}$, in which the group (XXV) can contain the C═C double bond also in position-isomeric arrangements on the branched carbon atom, for example, as —C═$CH_2$, by acid-catalyzed hydration obeying the Markownikoff Rule, into the xanthines of formulas (IX) to (XVI) pursuant to the invention, and if desired, then coverting the tertiary hydroxyalkylxanthines of formulas Ib' and if obtained pursuant to the invention by methods e) to h) that have a hydrogen atom in the 1- or 7-position, optionally in the presence of basic media or in the form of their salts, with the alkylating agents of formula (VIII) or (Xa) or (XIII), into the trisubstituted compounds of formulas (X) or (XI) or (XV), in which $R^2$, $R^4$, $R^5$, $R^{15}$, and n in the formulas above have the meanings indicated above.

The 3-alkylated mono- or dioxoalkyl-(XIXa), -(ω-haloalkyl) (XIXb), -(ω-alkoxycarbonylalkyl)-(XIXc), and -alkenylxanthines (XIXd) needed for this as starting materials are either known or can be prepared readily, for example, from the 3-alkyl-xanthines (VII:) and the sulfonyloxy- or haloketones (XVII) and (XVIII), ω-haloalkylsulfonates, or 1,ω-dihaloalkanes (cf., for example: V. B. Kalcheva et al., Journal fur prakt. Chemie 327 (1985) pp. 165–168), ω-sulfonyloxy or ω-halocarboxylic acid alkyl esters or sulfonyloxy or haloalkenes corresponding to formula (XXV) under the reaction conditions previously described in detail for the alkylation of mono- and disubstitued xanthines with the compounds of formulas (VIII) and (Xa).

In the organometallic reactions of the xanthines (XIXa) and (XIXc) functionalized in the $R^9$ and $R^{10}$ groups, the procedure is the same in principle as described for the preparation of the tertiary alcohols of formula (VIII) used as alkylating agents. Thus, the reductive alkylation of the ketones (XIXa) and of the esters (XIXC) can take place, for example, with alkylpotassium, -sodium, -lithium, -magnesium, -zinc, -cadmium, -aluminum, and -tin compounds. The recently recommended alkyltitanium and -zirconium compounds (D. Seebach et al., Agnew, Chem. 95 (1983), pp. 12–26) can also be used. However, since the alkylmetal compounds of sodium and potassium have a tendency toward side reactions because of their high reactivity and those of zinc and cadmium are relatively sluggish, the alkyllithium and -magnesium (Grignard) compounds are ordinarily preferred.

The strong nucleophilic organometallic compounds are very sensitive to hydrolysis and oxidation. Their safe handling therefore requires working in anhydrous medium, optionally under an inert gas atmosphere. The usual solvents or distributing agents are primarily those that are suitable also for the preparation of the alkylmetal compounds. Practical examples are especially ethers with one or more ether oxygen atoms, for example diethyl, dipropyl, dibutyl, or diisoamyl ether, 1,2-dimethoxyethane, tetrahydrofuran, dioxane, tetrahydropyran, furan, and anisole, and aliphatic or aromatic hydrocarbons, such as petroleum ether, cyclohexane, benzene, toluene, xylenes, diethylbenzenes, and tetrahydronaphthalene; however, tertiary amines, such as triethylamine, or dipolar aprotic solvents, such as hexamethylphosphoric triamide, as well as mixtures of the solvents mentioned can also be used successfully. The reaction of the carbonyl compounds (XIXa) and (XIXC) with the Grignard compounds with the formula $R^4$-MgHal can also beneficially be carried out by placing the organometallic compound in an ether and adding the ketone or the ester dropwise as a solution in dischloromethane or 1,2-dicholoroethane. An addition of magnesium bromide is frequently recommended, which is able to increase the nucleophilicity of the organometallic compound because of its participation in the complex cyclic transition state.

The ketone or ester and the organometallic compound are generally combined at temperatures between −20° C. and 100° C., preferably between 0° C. and 60°, or at room temperature without external cooling, with the alkylmetal compound ordinarily being used in slight excess. The reaction is then ordinarily completed by brief heating under reflux, for which times of several minutes to a few hours are generally adequate. The alkanolate formed is preferably decomposed with aqueous ammonium chloride solution or dilute acetic acid.

Metallic magnesium and lithium are primarily suitable for the metallation of the ω-haloalkylxanthines (XIXb). On the other hand, the replacement of the halogen atom with lithium, which is also possible using organolithium reagents, generally 1-butyl-, 2-butyl-, t-butyl-, or phenyllithium, plays a subordinate role. However, use is made especially of the Grignard compounds, advantageously preparing them in the ethers, hydrocarbons, tertiary amines, or aprotic solvents listed as particularly suitable for the reaction of the xanthines (XIXa) and (XIXc) with alkylmetal compounds, at temperatures between 25° and 125° C., preferably below 100° C. If the metallation reaction is carried out in hydrocarbons, then the addition of an ether, such as tetrahydrofuran, or a tertiary amine, such as triethylamine, in stoichiometric amount frequently proves useful. The use of catalysts, such as butanol, aluminum chloride, silicon tetrachloride, tetrachloromethane, and aluminum or magnesium alcoholates, may also be helpful. In the halogen-metal exchange the chlorides ordinarily react more slowly than the corresponding bromides and iodides, but as a rule they provide better yields of organometallic compound. To accelerate the beginning of the reaction, the addition of some magnesium bromide, some grains of iodine, or several drops of bromine, tetrachloromethane, or methyl iodide with slight heating is frequently recommended. The Grignard compounds obtained are normally not isolated, but are reacted immediately with the ketones of formula (XXIII) under the reaction conditions described for the reductive alkylation of the xanthines (XIXa) and (XIXc).

The addition of water to the C=C double bond of the alkenylxanthines (XIXd) with the structural element of formula (XXV), in which the hydroxy group adds to the carbon atom with the fewer hydrogens to form tertiary alcohols according to the Markownikoff Rule, ordinarily occurs in aqueous solution or suspension in the presence of strong acids, such as sulfuric, nitric, or phosphoric acid. Hydrogen halides and sulfonic acids, such as trifluoromethanesulfonic acid, acid exchange resins, boron trifluoride complexes, or oxalic acid, can also be used as catalysts. However, it is preferred to operate in sulfuric acid, with an acid concentration of 50 to 65% and temperatures of 0° to 10° C. being sufficient as a rule. However, lower or higher acid concentration and/or reaction temperatures can sometimes also be used. In any case, the reaction temperatures should be kept as low as possible since the reverse dehydration to the olefin can be disturbingly significant above approximately 60° C.

The addition of a solvent inert to acids, such as 1,4-dioxane, benzene, or toluene, sometimes also provides benefits. Since esters can form as intermediates in the acid-catalyzed hydration, particularly when using the high acid concentrations, it is recommended to treat the reaction batch with a large amount of water with brief heating after the action of the acid for the purpose of ester hydrolysis, or to process the mixture in the alkaline range.

The experimental conditions for the optional conversion of the 1- and 7H-compounds (IX) or (XVI) pursuant to the invention into the trisubstituted xanthines of formulas (X) or (XV) by N-alkylation with the compounds (VIII) or (Xa) of (XIII) have already been described above in detail.

Depending on the chain length of the alkyl group $R^4$ (at least $C_2$) and/or the structure of a substituent $R^5$ (for example, 2-hydroxypropyl), the tertiary hydroxyalklyxanthines of formula (II) can have one or two asymmetric carbon atoms and can thus be present in stereoisomeric forms. This invention therefore concerns both the pure stereoisomeric compounds and their mixtures.

This invention will now be described in greater detail in the following Examples. More particularly, to demonstrate the effectiveness of the claimed invention, a compound of formula (II) was tested to demonstrate inhibition of the effects of GVHR in vivo. Though a variety of compounds within the general formulas (I) and (II) are effective, they will be exemplified with regard to pentoxifylline ("PTX") as a particularly preferred xanthine.

EXAMPLE 1

The Effect of Methylxanthine Derivatives on T-Cell Activation

When blood mononuclear cells from two unrelated individuals are cultured together, mutual stimulation occurs resulting in T cell activation and blastogenesis and ultimately in the generation of cytotoxic T cells and memory cells. This complex series of events, termed the mixed leukocyte reaction (MLR), requires genetic disparaties at the HLA-DR locus. Monocytic cells are needed for antigen processing and presentation. The MLR is thus measures lymphocyte recognition and response to non-self-antigens and serves as an in vitro representation of some of the cellular events associated with graft-versus-host disease (GVHD) and allograft rejection.

Pentoxyfylline (PTX), 1-(5-oxohexyl)-3,7-dimethylxanthine), can prevent endotoxin induced upregulation of TNF MRNA in U937 cells probably by decreasing transcription. Due to the potentially critical role of TNF in lymphocyte activation, the effects of PTX, its first metabolite (M1), and the related compound 7-ethoxymethyl-1-(5-hydroxy-5-methylhexyl)-3-methylxanthine, on T cell activation were assessed in an MLR and by phytohemagluttinin (PHA).

Figure 2:
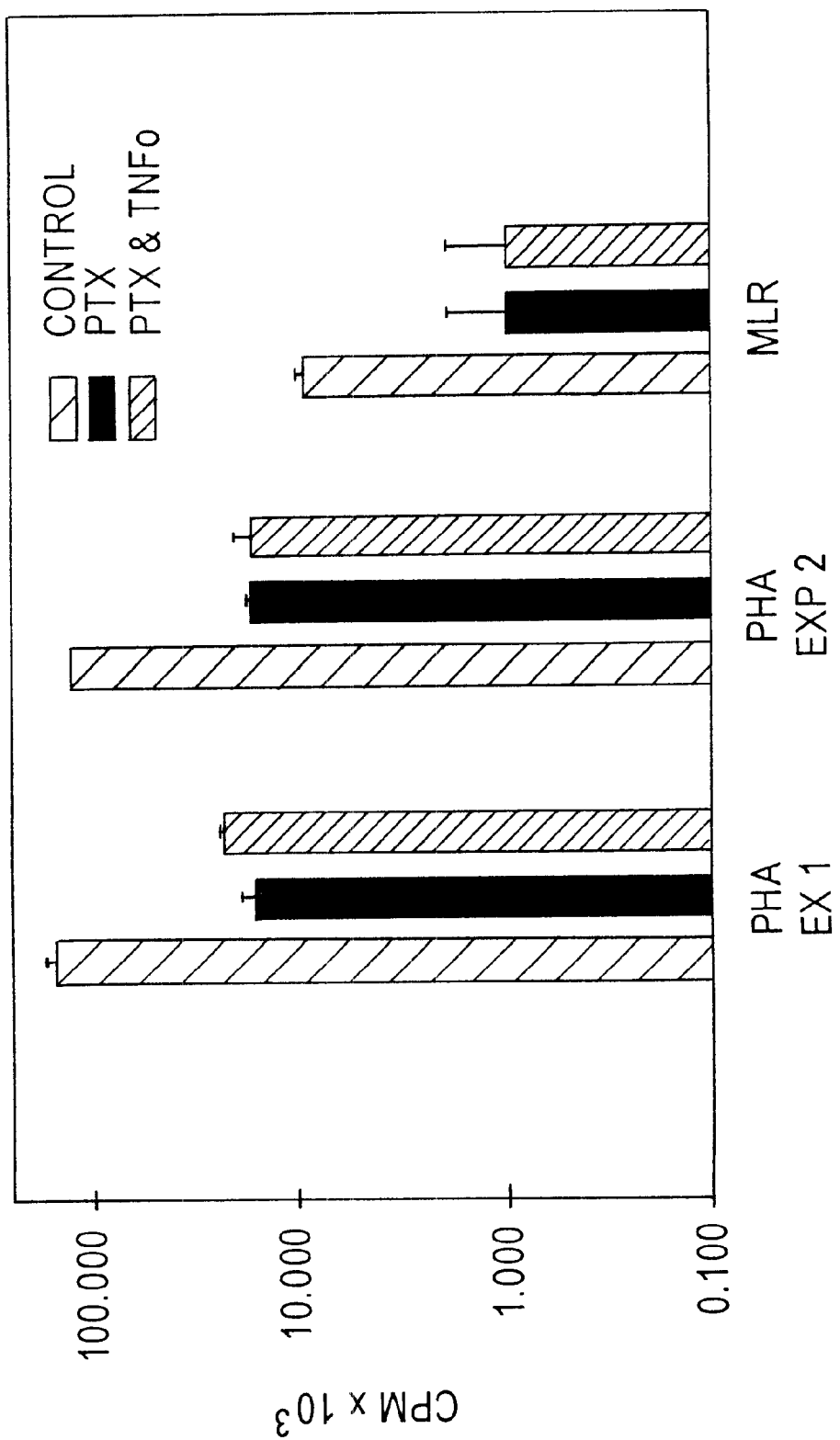
FIG. 2 shows the effect of adding recombinant human tumor necrosis factor (rhTNF), 200 U/ml., to either PHA-stimulated mononuclear cells (2 independent experiments) or a bidirectional MLR.

FIG. 2 shows the effect of PTX and 7-ethoxymethyl-1-(5-hydroxy-5-methylhexyl)-3-methylxanthigne on the expression of T cell activation antigens analyzed by direct immunofluorescence after 6 days of culture in a bidirectional MLR. The following fluorescein isothyoc:yanate (FITC) or phycoerythrin (PE) conjugated antibodies were used: IgGl and IgG2a isotype controls, anti-HLe-1 (CD45), anti-LeuM3 (CD14). anti-Leu4(cd3), anti-IL2-receptor (CD25), anti-transferrin receptor (CD71), anti-HLA-DR, and anti-Leu23 (CD69). (All antibodies were from Becton-Dickinson, San Jose, Calif.) Staining was performed using Manufacturer's recommendations (20 l antibody/$10^6$ cells in 0.1 ml of phosphate buffered saline for 20' at room temperature). The cells were washed twice, resuspended and analyzed on a Becton-Dickinson FACSan flow cytometer operating under Consort 30 software. The lymphocyte analysis gate was determined on the basis of forward scatter and side scatter and confirmed by examination of two-color immunofluorescence display for CD4S and CD14. Data are presented as the percentage of cells with fluorescence greater than that of the appropriate isotype control.

FIG. 2 shows the effect of adding recombinant human tumor necrosis factor (rhTNF), 200 U/ml, to either PHA-stimulated mononuclear cells (2 independent experiments) or a bidirectional MLR. rhTNF (Genentech Corp.) was added at the inception of the culture to microtitre wells containing PTX. Controls including PTX alone (shown) and TNF alone (not shown). TNF did not stimulate mononuclear cells grown without PRA or allogeneic cells. Nor did, it inhibit $^3$Htdr incorporation in cells culture without PTX. Results are the means SD of triplicate wells.

When blood mononuclear cells from normal individuals were cultured alone, with PHA, and in bidirectional MLR's with and without PTX or 3 related compounds, PTX, its M1 metabolite, and 7-ethoxymethyl-1-(5-hydroxy-5-methylhexyl)-3-methylxanthine [compound 1] actively inhibited $^3$Htdr uptake after 6 days in culture in a concentration dependent manner as shown in Table 1.

TABLE 1

Inhibition of tritiated thymidine uptake expressed as a percentage of control cultures

| CONTROL | PHA (% CONTROL) (100) | MLR (% CONTROL) (100) |
| --- | --- | --- |
| PTX | 49.2 16.2 | 33.4 12.2 |
| M1 | 11.2 | 6.1 |
| Compound 1 | 43.8 9.4 | 35.7 4.1 |
| Compound 2 | 78.6 20.7 | 73.4 11.9 |
| Denbufylline | 103.9 26.9 | 103.5 5.9 |

Compound 1 = 7-ethoxymethyl-1-(5-hydroxy-5-methylhexyl)-3-methyexanthine
Compound 2 = 1-(5-hydroxy-5-methylhexyl)-3-methylxanthine
Denbufylline = 7-acetonyl-1,3-dibutyl-xanthine All values except those for M1 represent: the means of calculated results from 6 to 8 independent experiments. The M1 results are the average of 2 independent experiments.

With PTX and M1, the highest concentration tested (1 mM) was most effective, but significant suppression of $^3$Htdr uptake was observed at concentrations as low as 0.01 mM. There was no decrease in cell viability in the test cultures as assessed by trypan blue dye exclusion (cell viability >95% in all groups). When whole cellular RNA was extracted from an MLR, there was some upregulation of FNF MRNA compared to cultures of the mononuclear cells cultured individually. However, basal levels of TNF mRNA were readily detectable, possibly due to some activation during the culture period. This was also reflected by significant levels of $^3$Htdr uptake. The level of TNF mRNA was significantly decreased in the MLR's containing PTX and 7-ethoxymethyl-1-(5-hydroxy-5-methylhexyl)-3-methylxanthine (FIG. 1). The diminution in response to PHA and the MLR observed with PTX was not abrogated by the addition of recombinant human TNP at a concentrations of 200U/ml.

During T cell activation, there is increased expression of certain cell surface determinants which can serve as markers of activation. FIG. 2 shows the effect of PTX and 7-ethoxymethyl-1-(5-hydroxy-5-methylhexyl)-3-methylxanthine on expression of a CD2, a non-activation dependent pan-T antigen and 4 activation dependent antigens. Although there were no differences in the expression of CD2 between the groups, both 7-ethoxymethyl-1-(5-hydroxy-5-methylhexyl)-3-methylxanthine and PTX decreased the expression of HLA-DR, the transferrin receptor, the IL-2 receptor, and CD69 in bidirectional MLR cultures to near the levels observed in mononuclear cells from a single donor cultured for 6 days.

PTX, one of its major metabolites, M1, and an analogue, 7-ethoxymethyl-1-(5-hydroxy-5-methylhexyl-3-methylxanthine [compound 1], each suppressed T cell activation and proliferation both by direct stimulation with PHA and in an MLR. As previously shown in endotoxin stimulated monocytic cells, PTX decreased both TNF MRNA expression and release of the cytokine into the culture medium. The PTX suppression of the MLR was not reversed by the addition excess rhTNF suggesting that other genes important in T cell activation were also affected by PTX. For example, the data indicate that PTX decreases antigen-induced upregulation of the IL-2 receptor and may thus blunt autocrine stimulation by IL-2. While PTX blocks endotoxin-induced production of TNF mRNA in monocytic cells, its effect on TNF production by activated T cells had not been previously described.

The present in vitro data suggest that selected methylxanthine derivatives, which have few deleterious side effects in viva, are likely to have clinically useful immunosuppressive properties.

In summary, entry of antigen into the body triggers the immune system. The antigen is trapped by accessory cells, and its antigenic determinants are presented to B and T lymphocytes. Antigen-stimulated B and T cells interact with one another to trigger proliferation and differentiation into effector cells. These terminally differentiated cells and their products combine with the antigen and initiate mechanisms for its elimination. The use of xanthines according to this invention makes it possible to use xanthine as immunosuppressive agents by suppressing the activation of lymphocytes. Lymphocyte activity can thus be regulated in such a way that hypersensitivity diseases, of the immune system can be effectively treated. As a result, the prognosis of patients afflicted with autoimmune diseases should improve.

What is claimed is:

1. A method of inhibiting an allograft reaction, which is manifested as host versus graft rejection or graft versus host rejection, in a human patient having received an allograft, comprising administering to said human patient an allograft reaction-inhibiting effective amount of pentoxifylline.

2. The method of claim 1, wherein said allograft reaction is host versus graft rejection.

3. The method of claim 1, wherein said allograft reaction is graft versus host rejection.

4. The method of claim 1, further comprising administering recombinant human GM-CSF to the patient.

5. The method of claim 1, wherein administration of pentoxifylline suppresses activation of effector cells other than effector inflammatory cells.

6. The method of claim 5, wherein the effector cells are lymphocytes selected from a group consisting of T helper cells, T cytotoxic cells, T suppressor cells, natural killer cells, killer cells responsible for antibody-dependent, cell-mediated toxicity, T delayed hypersensitivity cells, B lymphocytes and subsets of the foregoing lymphocytes.

7. The method of claim 1, wherein the allograft reaction results from a transfer of immunologically competent cells from one individual to the patient.

8. The method of claim 7, wherein the patient is immunologically incompetent or suppressed.

9. The method of claim 8, wherein the immunologically competent cells are from lymphoid tissues.

10. The method of claim 9, wherein the lymphoid tissues are bone marrow, lymph nodes, spleen, thymus or liver.

11. The method of claim 1, wherein the patient is a clinical marrow transplant recipient.

12. A method of treating or preventing graft versus host rejection in a patient having an allograft, comprising administering to the patient an amount of pentoxifylline which is effective to treat or prevent the graft versus host rejection.

13. The method of claim 12, wherein administration of pentoxifylline suppresses activation of effector cells other than effector inflammatory cells.

14. The method of claim 13, wherein the effector cells are lymphocytes selected from a group consisting of T helper cells, T cytotoxic cells, T suppressor cells, natural killer cells, killer cells responsible for antibody-dependent, cell-mediated toxicity, 1 delayed hypersensitivity cells, B lymphocytes and subsets of the foregoing lymphocytes.

15. The method of claim 12, wherein the allograft reaction results from a transfer of immunologically competent cells from one individual to the patient.

16. The method of claim 15, wherein the patient is immunologically incompetent or suppressed.

17. The method of claim 16, wherein the immunologically competent cells are from lymphoid tissues.

18. The method of claim 17, wherein the lymphoid tissues are bone marrow, lymph nodes, spleen, thymus or liver.

19. The method of claim 17, wherein the patient is a clinical marrow transplant recipient.

* * * * *